(12) United States Patent
Kopp

(10) Patent No.: US 10,548,676 B2
(45) Date of Patent: Feb. 4, 2020

(54) SURGICAL ASSEMBLIES AND METHODS OF USE

(71) Applicant: Covidien LP, Mansfield, MA (US)

(72) Inventor: Brock Kopp, Branford, CT (US)

(73) Assignee: Covidien LP, Mansfield, MA (US)

(*) Notice: Subject to any disclaimer, the term of this patent is extended or adjusted under 35 U.S.C. 154(b) by 44 days.

(21) Appl. No.: 15/548,311

(22) PCT Filed: Jan. 20, 2016

(86) PCT No.: PCT/US2016/014056
§ 371 (c)(1),
(2) Date: Aug. 2, 2017

(87) PCT Pub. No.: WO2016/133636
PCT Pub. Date: Aug. 25, 2016

(65) Prior Publication Data
US 2018/0000549 A1    Jan. 4, 2018

Related U.S. Application Data

(60) Provisional application No. 62/118,248, filed on Feb. 19, 2015.

(51) Int. Cl.
*A61B 34/00*    (2016.01)
*A61B 34/35*    (2016.01)
*A61B 17/00*    (2006.01)

(52) U.S. Cl.
CPC ........ *A61B 34/35* (2016.02); *A61B 17/00234* (2013.01); *A61B 2017/00314* (2013.01);
(Continued)

(58) Field of Classification Search
CPC . A61B 17/28; A61B 2034/301; A61B 17/701; A61B 17/7011; A61B 2017/3443;
(Continued)

(56) References Cited

U.S. PATENT DOCUMENTS 5,658,272 A * 8/1997 Hasson .............. A61B 17/3403
606/1
7,108,688 B2   9/2006 Jensen
(Continued)

OTHER PUBLICATIONS

International Search Report for (PCT/US2016/014056) date of completion is May 12, 2016 (5 pages).
(Continued)

*Primary Examiner* — Michael W Kahelin
*Assistant Examiner* — Sana Sahand

(57) ABSTRACT

A surgical assembly includes a surgical instrument and a holder. The surgical instrument includes an elongate body and an end effector. The elongate body has a proximal portion and a distal portion that defines a longitudinal axis therealong. The proximal portion is movable relative to the distal portion between a first condition and a second condition. In the first condition, the proximal portion is parallel to the longitudinal axis. In the second condition, the proximal portion is non-parallel to the longitudinal axis. The holder is configured to be coupled to the elongate body to selectively retain the proximal portion of the elongate body in the first condition.

16 Claims, 3 Drawing Sheets

(52) U.S. Cl.
CPC ............... *A61B 2017/00398* (2013.01); *A61B 2017/00477* (2013.01); *A61B 2017/00862* (2013.01); *A61B 2017/00946* (2013.01)

(58) Field of Classification Search
CPC . A61B 2017/2927; A61B 90/11; A61B 34/35; A61B 34/70
See application file for complete search history.

(56) References Cited

U.S. PATENT DOCUMENTS

| | | | | |
|---|---|---|---|---|
| 7,608,083 | B2* | 10/2009 | Lee | A61B 34/20 606/1 |
| 7,789,875 | B2 | 9/2010 | Brock et al. | |
| 8,231,160 | B2 | 7/2012 | Jo et al. | |
| 8,236,010 | B2* | 8/2012 | Ortiz | A61B 17/068 606/142 |
| 8,282,653 | B2 | 10/2012 | Nelson et al. | |
| 2002/0133173 | A1* | 9/2002 | Brock | A61B 17/0469 606/130 |
| 2005/0119638 | A1* | 6/2005 | Jensen | B25J 9/1065 606/1 |
| 2007/0021737 | A1* | 1/2007 | Lee | A61B 17/062 606/1 |
| 2007/0250113 | A1* | 10/2007 | Hegeman | A61B 1/0055 606/207 |
| 2009/0240259 | A1* | 9/2009 | Nelson | A61B 34/30 606/130 |
| 2011/0160539 | A1* | 6/2011 | Robertson | A61B 17/3421 600/204 |
| 2012/0253326 | A1 | 10/2012 | Kleyman | |
| 2013/0123783 | A1* | 5/2013 | Marczyk | A61B 17/29 606/45 |
| 2013/0144306 | A1* | 6/2013 | Stefanchik | A61B 17/29 606/130 |
| 2014/0180308 | A1* | 6/2014 | von Grunberg | A61B 90/11 606/130 |
| 2017/0035402 | A1* | 2/2017 | Matsui | A61B 17/34 |
| 2017/0258539 | A1* | 9/2017 | Cohen | A61B 34/70 |

OTHER PUBLICATIONS

European Search Report dated Oct. 5, 2018, corresponding to European Application No. 16752767.0; 8 pages.

* cited by examiner

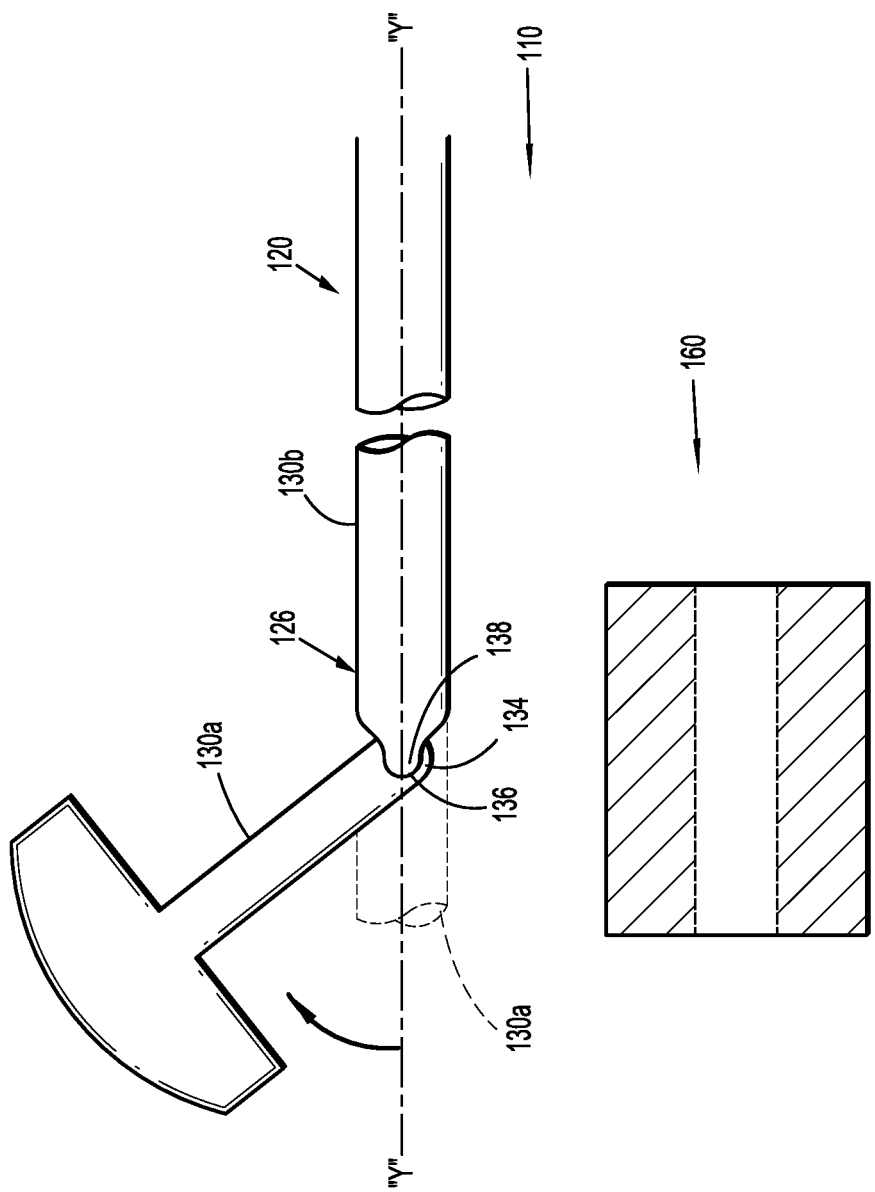

SURGICAL ASSEMBLIES AND METHODS OF USE

CROSS-REFERENCE TO RELATED APPLICATIONS

This application is a U.S. National Stage Application filed under 35 U.S.C. § 371(a) of International Patent Application Ser. No. PCT/US2016/014056, filed Jan. 20, 2016, which claims the benefit of and priority to U.S. Provisional Patent Application Ser. No. 62/118,248, filed Feb. 19, 2015, the entire disclosure of which is incorporated by reference herein.

BACKGROUND

Various types of surgical instruments used to endoscopically treat tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument. Typically, surgical stapling instruments include an end effector having an anvil assembly and a cartridge assembly for supporting an array of surgical staples, an approximation mechanism for approximating the cartridge and anvil assemblies, and a firing mechanism for ejecting the surgical staples from the cartridge assembly. Other examples of surgical instruments used to endoscopically treat or operate on tissue include surgical forceps, graspers and the like.

During laparoscopic or endoscopic surgical procedures, access to a surgical site is achieved through a small incision or through a narrow cannula inserted through a small entrance wound in a patient. Because of limited area available to access the surgical site and the large size of the surgical instrument, it may be somewhat involved to effectively remove the surgical instrument from the surgical site after surgery. Additionally, when employing a surgical robotic arm to perform surgical procedures, withdrawal of the surgical instrument from the robotic arm may pose an issue due to large size of the surgical instrument and/or the robustness of the surgical robotic arm.

Accordingly, a need exists for an improved surgical instrument, which can be selectively reduced in overall length to occupy less space and to increase ease of maneuverability during insertion and withdrawal from a surgical site.

SUMMARY

In one aspect of the present disclosure, an embodiment of a surgical assembly includes a surgical instrument and a holder. The surgical instrument includes an elongate body and an end effector. The elongate body has a proximal portion and a distal portion that defines a longitudinal axis therealong. The proximal portion is configured to be coupled to an actuator. The proximal portion is movable relative to the distal portion between a first condition and a second condition. In the first condition, the proximal portion is parallel to the longitudinal axis. In the second condition, the proximal portion is non-parallel to the longitudinal axis. The end effector extends distally from the distal portion of the elongate body and is configured to be operably coupled to an actuator. The holder is configured to be coupled to the elongate body to selectively retain the proximal portion of the elongate body in the first condition.

In some embodiments, the holder may define a channel therein. The channel extends longitudinally through the holder and is configured for receipt of the proximal portion of the elongate body.

It is contemplated that the holder may have a mating feature extending into the channel. The proximal portion of the elongate body may also have a mating feature configured to matingly engage the mating feature of the holder.

It is envisioned that the holder may be cylindrical and slidable along the elongate body.

In some aspects, the holder may be configured to couple to the proximal portion of the elongate body in a snap-fit engagement.

In some embodiments, the proximal portion of the elongate body may be more flexible than the distal portion of the elongate body.

In some aspects, the proximal portion of the elongate body may include a plurality of joints. A first joint may have a knuckle, and a second joint may have a clevis pivotably engaged to the knuckle of the first joint.

It is contemplated that the proximal portion of the elongate body may have a non-linear configuration in the second condition.

It is envisioned that the proximal portion of the elongate body may be pivotably connected to the distal portion of the elongate body. A proximal end of the distal portion may have a clevis, and a distal end of the proximal portion may be pivotably connected to the clevis.

In some aspects, the proximal portion of the elongate body may have a linear configuration when in the second condition.

In another aspect of the present disclosure, a method of performing a surgical procedure is provided. The method includes providing a surgical assembly, which includes a surgical instrument and a holder. The surgical instrument includes an elongate body and an end effector. The elongate body has a proximal portion and a distal portion that defines a longitudinal axis. The proximal portion is configured to be coupled to an actuator. The proximal portion is movable relative to the distal portion between a first condition and a second condition. In the first condition, the proximal portion is parallel to the longitudinal axis. In the second condition, the proximal portion is non-parallel to the longitudinal axis. The end effector extends distally from the distal portion of the elongate body and is configured to be operably coupled to an actuator. The holder is configured to be coupled to the elongate body to selectively retain the proximal portion of the elongate body in the first condition. The holder is positioned on the proximal portion of the elongate body of the surgical instrument to selectively retain the proximal portion of the elongate body in the first condition.

In some embodiments, positioning the holder on the proximal portion of the elongate body of the surgical instrument may move the proximal portion of the elongate body of the surgical instrument from the second condition to the first condition. It is contemplated that positioning the holder on the proximal portion of the elongate body of the surgical instrument may include sliding the surgical instrument within the holder.

It is envisioned that the method may further include withdrawing, in a proximal direction, the surgical instrument from the holder, and moving the proximal portion of the elongate body of the surgical instrument from the first condition to the second condition to reduce an overall length of the surgical instrument.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

The above and other aspects, features, and advantages of the present disclosure will become more apparent in light of the following detailed description when taken in conjunction with the accompanying drawings in which:

FIG. 4 is a schematic side view of another embodiment of a surgical assembly including a surgical instrument in a second, non-linear condition and a holder, and also illustrating in phantom the surgical instrument in a first, linear condition.

Figure 1:
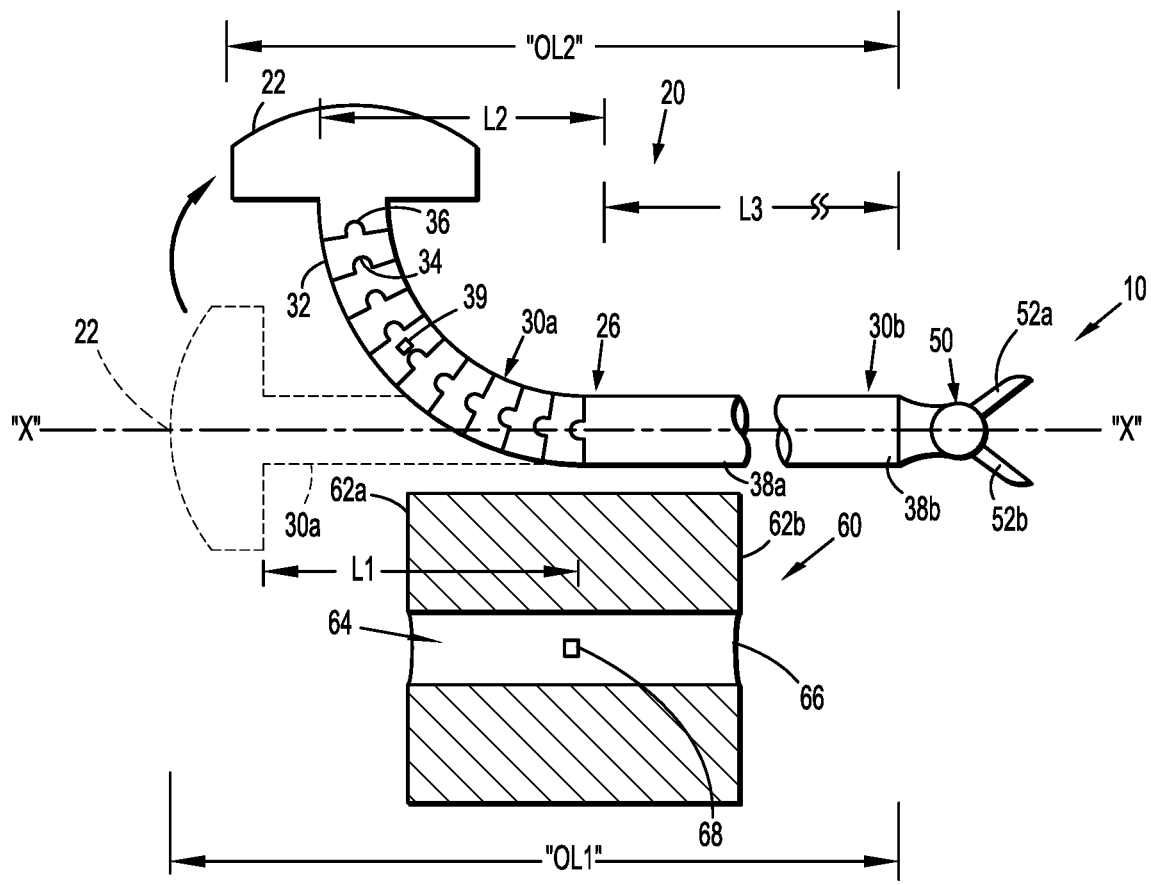
FIG. 1 is a schematic side view of an embodiment of a surgical assembly including a surgical instrument in a second, non-linear condition and a holder separated from the surgical instrument, and also illustrating in phantom the surgical instrument in a first, linear condition.

Other features of the present disclosure will become apparent from the following detailed description, taken in conjunction with the accompanying drawings, which illustrate, by way of example, the principles of the present application.

DETAILED DESCRIPTION

Embodiments of the presently disclosed surgical assemblies are described in detail with reference to the drawings, in which like reference numerals designate identical or corresponding elements in each of the several views. As used herein, the term "distal" refers to that portion of the surgical assemblies, or components thereof, farther from the user, while the term "proximal" refers to that portion of the surgical assemblies, or components thereof, closer to the user.

As will be described in detail below, provided is a surgical assembly that includes a surgical instrument and a holder. The surgical instrument has a proximal portion that is movable relative to a distal portion of the surgical instrument to selectively reduce an overall length of the surgical instrument. The holder can be selectively coupled to the surgical instrument to retain the surgical instrument in its original, lengthened condition, as will be described in detail below.

Figure 2:
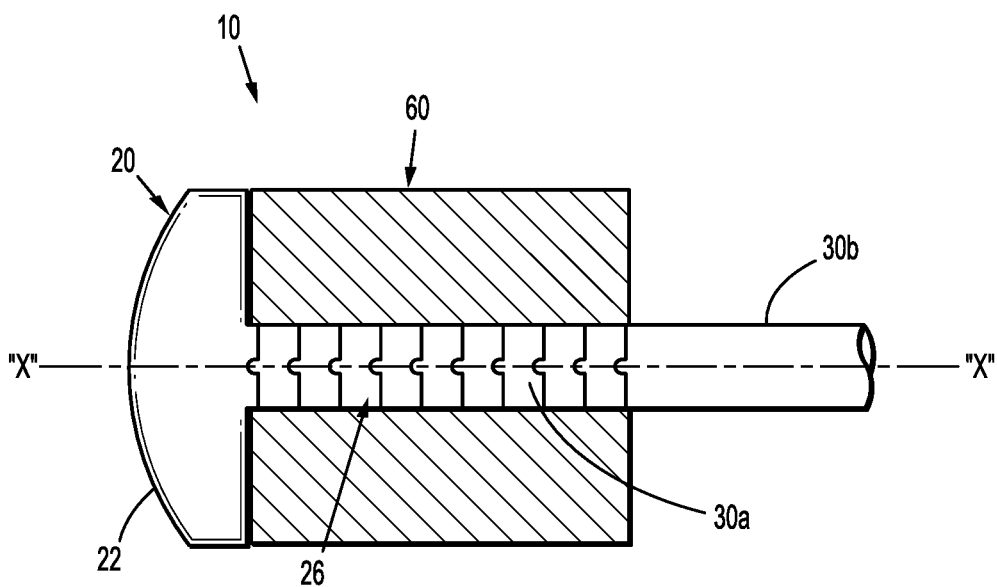
FIG. 2 is a schematic side view of the surgical assembly of FIG. 1 with the holder coupled to the surgical instrument, illustrating the surgical instrument in the first, linear condition.

Referring now to FIGS. 1 and 2, a surgical assembly is shown and generally designated by reference numeral 10. Surgical assembly 10 includes a surgical instrument, such as, for example, an electromechanical instrument 20, and a holder 60. Electromechanical instrument 20 generally includes an actuator 22, an elongate body 26 extending distally from actuator 22, and an end effector 50 operably coupled to a distal end of elongate body 26.

Actuator 22 of electromechanical instrument 20 may be in the form of a handle assembly configured to be gripped by a clinician to manipulate electromechanical instrument 20. Actuator 22 actuates functions of end effector 50. In some embodiments, actuator 22 may include a finger-actuated switch or trigger that when actuated activates motors (not shown) disposed in actuator 22 to effect operation of end effector 50. Actuator 22 has driven members (not shown) extending distally therefrom and through elongate body 26 of electromechanical instrument 20 to operably couple to various components of end effector 50 such that rotation and/or axial movement of each driven member effects actuation of various functions of end effector 50.

In some embodiments, instead of actuator 22 being in the form of a handle assembly as illustrated in FIG. 1, actuator 22 may alternately be an instrument drive unit (not shown) that directly couples to elongate body 26 of electromechanical instrument 20. The instrument drive unit may include motors for driving a rotation of the driven members (not shown) of electromechanical instrument 20. The instrument drive unit may be coupled to a surgical robotic arm (FIG. 3) used to move electromechanical instrument 20 and to actuate functions of end effector 50 of electromechanical instrument 20 via telemanipulation using manual input devices (not shown).

For a detailed discussion of the construction and operation of a robotic surgical system, reference may be made to U.S. Patent Application Publication No. 2012/0116416, filed on Nov. 3, 2011, entitled "Medical Workstation," the entire contents of which are incorporated by reference herein.

With continued reference to FIGS. 1 and 2, elongate body 26 of electromechanical instrument 20 has a proximal portion 30a and a distal portion 30b. Distal portion 30b defines a longitudinal axis "X." Proximal portion 30a is more flexible than distal portion 30b of elongate body 26 such that proximal portion 30a is movable relative to distal portion 30b between a first condition, such as, for example, a linear configuration, and various second conditions, such as, for example, non-linear, or bent configurations. As shown in phantom in FIG. 1, in the linear configuration, proximal portion 30a is parallel to the longitudinal axis "X" defined by distal portion 30b of elongate body 26 and has a first length "L1." As also shown in FIG. 1, in the non-linear configurations, proximal portion 30a is non-parallel with respect to the longitudinal axis "X" defined by distal portion 30b of elongate body 26 and has a second length "L2," less than the first length "L1."

Proximal portion 30a is flexible due to being comprised of a plurality of interconnected and relatively movable joints 32. Each joint 32 has a disc-shaped configuration and a clevis 34 disposed on a distal side of the joint 32 and a knuckle 36 disposed on a proximal side of the joint 32. Each knuckle 36 operatively engages clevis 34 of an adjacently disposed joint 32 such that joints 32 are pivotable relative to one another. Each joint 32 may, for example, define a central lumen (not shown) formed therein and a pair of opposed side lumens (not shown) formed on either side of the central lumen. A pair of articulation cables (not shown) may slidably extend through respective side lumens of joints 32. Distal ends of the articulation cables are connected to a distal-most joint of joints 32. Proximal portion 30a of elongate body 26 is moved between the linear configuration and the various non-linear configurations by moving either of the articulation cables in various directions relative to longitudinal axis "X." Alternately, joints 32 of proximal portion 30a may be pivoted relative to one another by a hand of a clinician.

In some embodiments, rather than proximal portion 30a being composed of joints 32, proximal portion 30a may be fabricated from a material capable of being deformed by a hand of a clinician during use thereof. Once deformed, the material properties of proximal portion 30a may cause proximal portion 30a to retain its deformed shape.

In some embodiments, an adapter (not shown) may be configured for removable attachment to elongate body 26 and to end effector 50, or elongate body 26 itself may form a removable adapter. Such adapters may include an adapter for connection to a manually powered handle assembly. Additionally or alternatively, adapters permitting alternative elongate body lengths, rigid or flexible elongate bodies, steerable elongate bodies, elongate bodies in various shapes, etc., can be provided for connecting end effector 50 to actuator 22. Elongate body 26 can be configured as a removable and replaceable adapter and can include an interface between proximal portion 30a of elongate body 26 and a distal end of actuator 22, providing coupling means for the particular end effector to be utilized.

Distal portion 30b of elongate body 26 has a linear configuration and a fixed length "L3," which is greater than the first length "L1" of proximal portion 30a of elongate body 26. As such, distal portion 30b is longer than proximal portion 30a. Distal portion 30b has a proximal end 38a and a distal end 38b each being disposed along longitudinal axis "X" of distal portion 30b of elongate body 26. Proximal end 38a of distal portion 30b has a knuckle 36 pivotably connected to clevis 34 of the distal-most joint 32 of proximal portion 30a. Distal end 38b of distal portion 30b has end effector 50 connected thereto. Distal portion 30b may be monolithically formed from a rigid material such that distal portion 30b resists being moved out of its linear configuration or having its length "L3" changed. It is contemplated that distal portion 30b may be fabricated from any suitable rigid material, such as, for example, various metals or plastics. As such, typical use of electromechanical instrument 20 should not alter the linear configuration of distal portion 30b.

As mentioned above, end effector 50 is operably coupled to distal end 38b of distal portion 30b of elongate body 26. End effector 50 generally includes a pair of opposing jaw members 52a, 52b. End effector 50 may be moved, by actuation of the driven members (not shown) extending from actuator 22, from an open configuration wherein tissue is receivable between jaw members 52a, 52b, and a closed configuration, wherein the tissue is clamped and/or treated. The opposing jaw members 52a, 52b may be electrically coupled to a cable (not shown), and to a generator (not shown), via respective suitable electrical wiring (not shown) extending through elongate body 26 of electromechanical instrument 20 and through actuator 22 to provide an electrical pathway to a pair of electrically conductive, tissue-engaging sealing plates (not shown) disposed on the opposing jaw members 52a, 52b. In some embodiments, end effector 50 may be in the form of various suitable other types of end effectors including endoscopic forceps, graspers, dissectors, other types of surgical stapling instruments, powered vessel sealing and/or cutting devices, etc.

With continued reference to FIGS. 1 and 2, surgical assembly 10 includes a holder 60 configured to receive and be coupled to electromechanical instrument 20 for selectively retaining electromechanical instrument 20 in the linear configuration, as will be described in detail below. Holder 60, similar to distal portion 30b of elongate body 26, has a linear configuration and is rigid such that holder 60 resists being moved out of its linear configuration. Holder 60 may be fabricated from various suitable materials, such as, for example, metals or plastics configured to retain their manufactured shape.

Holder 60 has a generally half-cylindrical shape. In particular, holder 60 has a c-shaped transverse cross-section configuration and a rectangular longitudinal cross-section configuration. In some embodiments, holder 60 may assume a variety of shapes and configurations, such as, for example, sheath-like, fully cylindrical, rectangular, triangular, or the like. Holder 60 has a proximal end 62a configured to abut actuator 22 and a distal end 62b configured to extend at least up to distal-most joint 32 of proximal portion 30a of elongate body 26 when elongate body 26 is disposed in or coupled to holder 60. As such, holder 60 has substantially the same length as proximal portion 30a to fully enshroud proximal portion 30a.

Holder 60 defines a channel or lumen 64 therein that extends longitudinally therethrough. Channel 64 is configured for slidable receipt or passage of elongate body 26 therein or therethrough. Holder 60 has an inner wall 66 that defines channel 64. Inner wall 66 has an arcuate configuration corresponding to the rounded configuration of proximal portion 30a of elongate body 26. Holder 60 may have a mating feature 68 extending into channel 64, and proximal portion 30a may have a mating feature 39 provided therein or thereon. Mating features 68, 39 are configured to matingly engage one another upon positioning holder 60 on proximal portion 30a of elongate body 26 to selectively fix holder 60 to elongate body 26. It is contemplated that inner wall 66 of holder 60 may have a plurality of mating features configured to matingly engage a plurality of respective mating features of proximal portion 30a of elongate body 26.

In some embodiments, mating feature 68 of holder 60 may be in the form of a resilient projection and the mating feature 39 of proximal portion 30a of elongate body 26 may be a recess configured for removable receipt of the resilient projection. It is further contemplated that holder 60 may couple to proximal portion 30a of elongate body 26 via frictional engagement, bayonet-type engagement, or snap-fit engagement rather than or in addition to using corresponding mating features.

Figure 3:
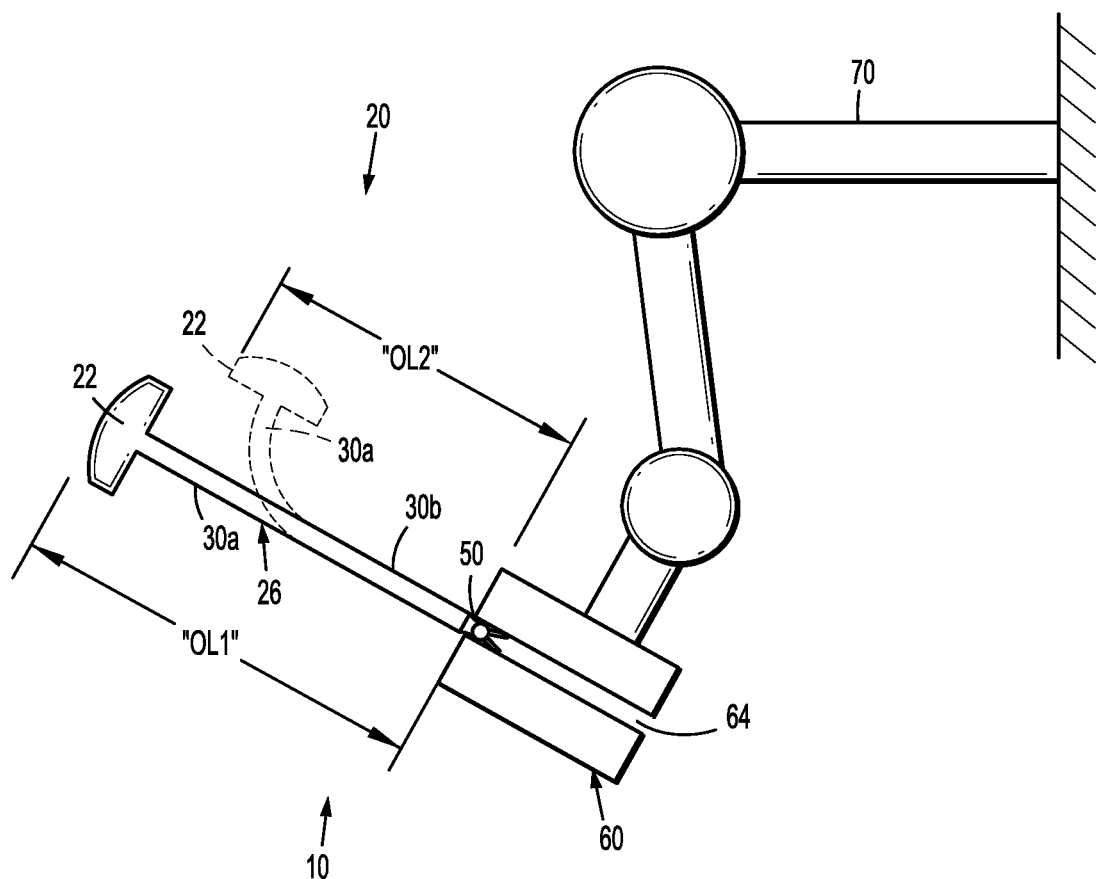
FIG. 3 is a schematic side view of the surgical assembly of FIG. 1 with the holder attached to a surgical robotic arm and with the surgical instrument in the first, linear condition, and also illustrating in phantom the surgical instrument in the second, non-linear condition.

With reference to FIG. 3, in one embodiment, holder 60 is configured to be coupled to a surgical robotic arm 70 to both selectively couple electromechanical instrument 20 to surgical robotic arm 70 and to retain proximal portion 30a of elongate body 26 of electromechanical instrument 20 in its linear configuration.

In operation, in an embodiment, electromechanical instrument 20 is guided within holder 60, which is attached to surgical robotic arm 70, as shown in FIG. 3. Upon inserting electromechanical instrument 20 within holder 60, proximal portion 30a of elongate body 26 is moved or bent by holder 60 to increase the length of proximal portion 30a from the second length "L2" to the first length "L1," as shown in FIG. 1. With proximal portion 30a in its linear condition, holder 60 may be coupled to proximal portion 30a of elongate body 60 to retain proximal portion 30a in its linear configuration as electromechanical instrument 20 is being used.

After use of electromechanical instrument 20, proximal portion 30a of elongate body 26 may be disengaged from holder 60 by removing or withdrawing, in a proximal direction, electromechanical instrument 20 from holder 60. With holder 60 disengaged from proximal portion 30a of elongate body 26, proximal portion 30a can be bent or flexed (e.g., via a hand of a clinician) relative to distal portion 30b of elongate body 26. In so doing, proximal portion 30a is moved from its linear configuration, in which proximal portion 30a of elongate body 26 is coaxial with longitudinal axis "X" of distal portion 30b, to one of the variety of non-linear configurations, in which proximal portion 30a of elongate body 26 is non-parallel (e.g., at an angle) or offset with respect to longitudinal axis "X" of distal portion 30b of elongate body 26. As proximal portion 30a is moved from the first condition to any one of the second conditions, an overall longitudinal length of surgical instrument 20 is reduced, as illustrated in FIGS. 1 and 3. Specifically, the overall longitudinal length of surgical instrument 20 is reduced from a first condition overall length "OL1" (first length "L1" of proximal portion 30a plus fixed length "L3" of distal portion 30b) to a second condition overall length "OL2" (second length "L2" of proximal portion 30a plus fixed length "L3" of distal portion 30b).

It can be appreciated that the more proximal portion 30a of elongate body 26 is bent, the shorter proximal portion 30a becomes. Alternately, proximal portion 30a may be moved to the second conditions via the translation of the cables through joints 32 of proximal portion 30a, as described in detail above.

Having reduced the overall longitudinal length of surgical instrument 20 from first condition overall length "OL1" to second condition overall length "OL2," by flexing proximal portion 30a relative to distal portion 30b, electromechanical instrument 20 can be removed from the surgical site with a decreased likelihood of a proximal end of electromechanical instrument 20 colliding with surgical equipment in the operating room, operating room staff, the ceiling, etc. Additionally, by reducing the overall length of electromechanical instrument 20, electromechanical instrument 20 may be removed from holder 60 and surgical robotic arm 70 without having to move or reorient surgical robotic arm 70. Further, with proximal portion 30a in one of the second conditions, in which it has a reduced overall length "OL2," it may be easier to store, package, and/or sterilize elongate body 26 of electromechanical instrument 20.

With reference to FIG. 4, another embodiment of a surgical assembly 110 is provided, which includes a surgical instrument 120, similar to electromechanical instrument 20 described above, and a holder 160, similar to holder 60 described above. Surgical instrument 120 includes an elongate body 126 having a proximal portion 130a and a distal portion 130b and defines a longitudinal axis "Y" therebetween. Unlike elongate body 26 described above with reference to FIGS. 1-3, both proximal and distal portions 130a, 130b of elongate body 126 are fabricated from non-flexible material configured to naturally retain their linear configurations during normal use of electromechanical instrument 120.

Proximal portion 130a of elongate body 126 is pivotably connected to distal portion 130b of elongate body 126. In particular, proximal portion 130a has a distal end having a knuckle 134, and distal portion 130b has a proximal end having a clevis 136. In some embodiments, the distal end of proximal potion 130a has the clevis 136 and the proximal end of distal portion 130b has the knuckle 134. Knuckle 134 is rotatably disposed within clevis 136. A pivot pin 138 extends through clevis 136 of distal portion 130b and knuckle 134 of proximal portion 130a such that proximal portion 130a is pivotable relative to distal portion 130b about a pivot axis defined through pivot pin 138.

In operation, prior to using electromechanical instrument 120 in a surgical procedure, holder 160 is coupled to proximal portion 130a of elongate body 126 and at least a portion of distal portion 130b to enshroud pivot pin 138. With holder 160 coupled to proximal and distal portions 130a, 130b of elongate body 126, proximal portion 130a is resisted from pivoting relative to distal portion 130b. Thus, elongate body 126 is retained in its linear configuration as electromechanical instrument 120 is being used.

After use of electromechanical instrument 120, holder 160 may be moved to no longer cover pivot pin 138 of elongate body 126 such that proximal portion 130a can be pivoted (e.g., via a hand of a clinician) relative to distal portion 130 about the pivot axis defined through pivot pin 138. In so doing, elongate body 26 is reconfigured from the first condition, in which proximal portion 130a of elongate body 126 is coaxial with distal portion 130b of elongate body 126, to one of a variety of non-linear configurations, as shown in FIG. 4, in which proximal portion 130a is non-parallel (e.g., at an angle) with respect to longitudinal axis "Y" of elongate body 126. As proximal portion 130a is moved from the first condition to any one of the second conditions, the longitudinal length of elongate body 126 is reduced. Due to the rigid nature of proximal portion 130a of elongate body 126, proximal portion 130a remains in a linear configuration after being pivoted to any one of its second conditions.

Each of the embodiments described above are provided for illustrative purposes only and it is within the concept of the present disclosure to include modifications and varying configurations without departing from the scope of the disclosure that is limited only by the claims included herewith.

The invention claimed is:

1. A surgical assembly, comprising:
  a surgical instrument including:
    an elongate body having a flexible proximal portion and a relatively rigid distal portion, the distal portion defining a longitudinal axis therealong, the proximal portion configured to be coupled between an actuator and the distal portion and being movable relative to the distal portion between a first condition, in which the proximal portion is linear and axially aligned with the distal portion, and at least one second condition, in which the proximal portion is non-linear, the proximal portion having a first length defined along the longitudinal axis when in the first condition; and
    an end effector extending distally from the distal portion of the elongate body and configured to be operably coupled to the actuator; and
  a holder configured to be coupled to the elongate body to selectively retain the proximal portion of the elongate body in the first condition, such that the holder bends the proximal portion of the elongate body from the at least one second condition to the first condition upon receiving the proximal portion of the elongate body, the holder defining a linear-shaped channel therein and which extends longitudinally through the holder, wherein the first length of the proximal portion of the elongate body is substantially the same as a length of the channel of the holder, such that the holder accommodates therein substantially the entire proximal portion of the elongate body when the proximal portion of the elongate body is received in the channel.

2. The surgical assembly according to claim 1, wherein the holder has a mating feature extending into the channel, and the proximal portion of the elongate body has a mating feature configured to matingly engage the mating feature of the holder.

3. The surgical assembly according to claim 1, wherein the holder is slidable along the elongate body.

4. The surgical assembly according to claim 1, wherein the holder is configured to couple to the proximal portion of the elongate body in a snap-fit engagement.

5. The surgical assembly according to claim 1, wherein the proximal portion of the elongate body includes a plurality of joints.

6. The surgical assembly according to claim 5, wherein a first joint of the plurality of joints has a knuckle, and a second joint of the plurality of joints has a clevis pivotably engaged to the knuckle of the first joint.

7. The surgical assembly according to claim 1, wherein the proximal portion of the elongate body is pivotably connected to the distal portion of the elongate body.

8. The surgical assembly according to claim 7, wherein a proximal end of the distal portion has a clevis, and a distal end of the proximal portion is pivotably connected to the clevis.

9. The surgical assembly according to claim 1, wherein the proximal portion has a second length defined along the longitudinal axis in the second condition, the second length being less than the first length.

10. The surgical assembly according to claim 9, wherein the distal portion has a length that is greater than the first length of the proximal portion.

11. A method of performing a surgical procedure, comprising:
providing a surgical instrument, including:
an elongate body having a flexible proximal portion and a relatively rigid distal portion, the distal portion defining a longitudinal axis therealong, the proximal portion configured to be coupled between an actuator and the distal portion and movable relative to the distal portion between a first condition, in which the proximal portion is linear and axially aligned with the distal portion, and at least one second condition, in which the proximal portion is non-linear; and
an end effector extending distally from the distal portion of the elongate body and configured to be operably coupled to the actuator;
providing a holder configured to be coupled to the elongate body; and
positioning the holder on the proximal portion of the elongate body of the surgical instrument, such that the holder accommodates therein substantially the entire proximal portion of the elongate body, wherein positioning the holder on the proximal portion of the elongate body bends the proximal portion of the elongate body from the at least one second condition to the first condition.

12. The method according to claim 11, wherein positioning the holder on the proximal portion of the elongate body of the surgical instrument includes sliding the surgical instrument within the holder.

13. The method according to claim 11, further comprising:
withdrawing, in a proximal direction, the surgical instrument from the holder; and
moving the proximal portion of the elongate body of the surgical instrument from the first condition to the at least one second condition to reduce an overall length of the surgical instrument.

14. The surgical assembly according to claim 1, wherein the distal portion of the elongate body is linear.

15. The surgical assembly according to claim 1, wherein the channel is configured to maintain its linear shape upon receiving the proximal portion of the elongate body when the proximal portion of the elongate body is in the at least one second condition.

16. The surgical assembly according to claim 1, wherein the actuator is attached to a proximal end of the elongate body, the holder having a proximally-facing surface configured to abut a distally-oriented surface of the actuator when the holder is coupled to the elongate body.

* * * * *